United States Patent
Hayamizu et al.

(10) Patent No.: US 6,396,579 B1
(45) Date of Patent: *May 28, 2002

(54) METHOD, APPARATUS, AND SYSTEM FOR INSPECTING TRANSPARENT OBJECTS

(75) Inventors: Mitsuru Hayamizu; Yoshihiko Nagata, both of Gunma-ken (JP)

(73) Assignee: Shin-Etsu Chemical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/036,967

(22) Filed: Mar. 9, 1998

(30) Foreign Application Priority Data

Mar. 10, 1997 (JP) .............................................. 9-070867
Jul. 25, 1997 (JP) .............................................. 9-215560

(51) Int. Cl.$^7$ ............................................... G01N 21/00
(52) U.S. Cl. ............................... 356/239.7; 356/239.8; 250/559.4; 250/559.41
(58) Field of Search ........................... 356/239.1, 239.7, 356/239.8; 250/559.4, 559.41, 559.42

(56) References Cited

U.S. PATENT DOCUMENTS

| | | | | | |
|---|---|---|---|---|---|
| 4,610,541 A | * | 9/1986 | Tanimoto et al. | ......... | 356/239.8 |
| 4,889,998 A | * | 12/1989 | Hayano et al. | .......... | 356/239.8 |
| 4,922,308 A | * | 5/1990 | Noguchi et al. | .......... | 356/239.8 |
| 4,966,457 A | * | 10/1990 | Hayano et al. | .............. | 356/237 |
| 4,999,510 A | * | 3/1991 | Hayano et al. | .......... | 356/239.8 |
| 5,452,079 A | * | 9/1995 | Okugawa | ................ | 250/559.42 |
| 5,598,262 A | * | 1/1997 | Jutard et al. | .............. | 356/239.1 |

FOREIGN PATENT DOCUMENTS

JP  4344447  12/1992  .......... G01N/21/88

\* cited by examiner

*Primary Examiner*—Frank G. Font
*Assistant Examiner*—Zandra Smith
(74) *Attorney, Agent, or Firm*—Hogan & Hartson L.L.P.

(57) ABSTRACT

In an inspection method for a transparent object, a transparent object is irradiated with light from a light source, and the surface or interior of the transparent object is inspected by observing transmitted light on the side of the transparent object that is opposite to the light source. An inspection apparatus for a transparent object includes a transparent-object-moving unit, an irradiation unit, and a detection unit. The transparent-object-moving unit moves a transparent object to an inspection position and fixes the transparent object in the inspection position. The irradiation unit emits light from a light source disposed on one side of the transparent object so as to irradiate light onto the transparent object fixed in the inspection position by the transparent-object-moving unit. The detection unit is located on the side of the transparent object opposite the light source and has a detector for detecting light that has been emitted from the light source and has passed through the transparent object. The inspection method and the inspection apparatus realize improved inspection accuracy and inspection efficiency.

2 Claims, 3 Drawing Sheets

METHOD, APPARATUS, AND SYSTEM FOR INSPECTING TRANSPARENT OBJECTS

BACKGROUND OF THE INVENTION

1. Field of the Invention

The present invention relates to a method, apparatus, and system for inspecting the surface or interior of transparent objects, such as quartz substrates for semiconductor devices, photomasks formed of quartz, and pellicle membranes used as dust protectors in the manufacture of semiconductor devices, such as LSIs an VLSIS, or liquid crystal display panels.

2. Description of the Related Art

In the manufacture of semiconductor devices, such as LSIs and VLSIs, or liquid crystal display panels, a semiconductor wafer or a liquid crystal material panel is irradiated, via a photomask, with light to thereby form circuit patterns on the wafer or liquid crystal material panel. If dust adheres to the photomask, the dust absorbs or deflects light, causing a transferred pattern to deform, a pattern edge to become rugged, or a white background to be blackishly smudged, and thus impairing dimensional accuracy, quality, or appearance. As a result, the manufacture of semiconductor devices or liquid crystal panels has involved a problem of impairment in the performance of manufactured semiconductor devices or liquid crystal panels or a decrease in manufacturing yield. Thus, the irradiation of a photomask with light is usually performed in a clean room. However, even in a clean room, keeping a photomask completely clean is difficult. Hence, there is employed a method of bonding a pellicle membrane having good transmission of exposure light onto the surface of a photomask for the purpose of protecting the mask surface from dust.

Through use of such a pellicle membrane, dust, if any, does not directly adhere to the surface of a photomask, but adheres to the pellicle membrane. Thus, by focusing light on the surface of the photomask where a circuit pattern exists, the dust adhering on the pellicle membrane has no effect on the transfer.

A transparent pellicle membrane for the above application is formed from a material having good transmission of visible light, such as nitrocellulose, cellulose acetate, modified polyvinyl alcohol, or a fluorine polymer, and is bonded onto a frame of aluminum alloy, stainless steel, polyethylene, or a like material. In bonding, a good solvent for the pellicle membrane is applied onto the frame, and then the pellicle membrane is placed on the frame, followed by air drying. Alternatively, the pellicle membrane is bonded onto the frame through use of adhesive such as an acrylic resin or epoxy resin. Further, on the opposite side of the frame are formed an adhesive layer formed from a polybutene resin, polyvinyl acetate resin, acrylic resin, or the like for adhesion to a photomask and a release layer for protection of the adhesive layer.

In view of the above-mentioned application of a pellicle membrane, both side surfaces and interior of the pellicle membrane must be free of foreign matter. Accordingly, the pellicle membrane undergoes strict inspection.

Also, quartz substrates for semiconductor devices and quartz photomasks bearing circuit patterns formed thereon must have transparency and be free of defects to a degree equal to or higher than in the case of pellicle membranes. Thus, the surfaces or interior of such transparent objects are strictly inspected for foreign matter.

Among conventional inspection methods for inspecting the surfaces or interior of transparent objects, a conventional inspection method for pellicle membranes is exemplified in FIG. 5. As shown in FIG. 5, a frame to which a pellicle membrane A is bonded is attached to a handling jig. In a darkroom for inspection, an inspector holds the jig and exposes the surface of the pellicle membrane A to a spotlight from a convergence lamp B, to thereby visually check for foreign matter adhering to the membrane, foreign matter or defects present inside the membrane, and wrinkles or scratches in the membrane.

In the conventional method, the spot-light from a convergence lamp reflected from the surface of the pellicle membrane or from the pellicle frame impinges on and dazzles the inspector's eyes, thus imposing a burden on the eyes. Accordingly, an adverse effect is imposed on the inspector's eyes, and the inspector cannot continue the inspection for a long period of time. Also, inspection efficiency is impaired, and the inspector is apt to overlook foreign matter, resulting in a possible impairment in detection accuracy. These unfavorable phenomena are observed not only in the inspection of pellicle membranes but also in the inspection of quartz substrates and photomasks. Thus, there has been eager demand for a solution to the problems.

Also, conventional inspection methods for inspecting the surfaces or interior of transparent objects other than the above-mentioned visual inspection method include a method in which a transparent object is irradiated with a laser beam, and light scattered by foreign matter present on the surface or in the interior of the object is detected by a photomultiplier (a first method), and a method in which foreign matter itself is magnified and detected through use of a charge coupled device camera (hereinafter referred to as a CCD camera) equipped with a microscope (a second method).

Further, there has been proposed an inspection method for inspecting a transparent object for defects through use of a CCD camera (Japanese Patent Application Laid-Open (kokai) No. 4-344447) (a third method). In this method, a transparent object is irradiated with light in three directions, and light scattered by a defect such as scratch or smudge is detected by a CCD camera.

The first method has an advantage of very high repeatability of measurement, but has the following disadvantage. For example, for the portion (several millimeters wide) of a pellicle membrane in the vicinity of or along a pellicle frame, measurement is disabled due to interference of the frame with a laser beam, scatter of the skirt portion of intensity distribution (usually Gaussian distribution) of a laser beam caused by the frame, the diffraction effect of a laser beam, or the like.

The second method is not practicable for the following reason. In order to detect foreign matter having a small grain size, the magnifying power of the microscope must be increased, and thus inspection takes a very long time.

The third method is suited for inspecting a transparent object for two-dimensional defects such as scratches and smudges, but cannot properly inspect a transparent object for three-dimensional defects, for example, foreign matter, because three-dimensional defects are significantly different from two-dimensional defects in terms of scattering of light. Further, in the case of inspecting a pellicle membrane, since the pellicle membrane has a frame attached at the periphery thereof, the portion of the pellicle membrane along the frame cannot be inspected by methods, such as the above-described third method, in which a transparent object is irradiated with light in three directions concurrently. Thus, this method is not suited for inspection of pellicles.

Accordingly, inspection apparatuses which carry out the methods described above involve the same problems.

SUMMARY OF THE INVENTION

The present invention has been accomplished in view of the problems, and an object of the invention is to provide an inspection method for transparent objects that enables easy and efficient visual inspection of a transparent object with a reduced burden on the inspector's eyes, as well as accurate judgment.

Another object of the present invention is to provide an inspection apparatus and inspection system which do not involve visual inspection and employ reflected light, and which is free from the above problems involved in conventional inspection apparatuses.

According to a first aspect of the present invention, there is provided an inspection method for a transparent object comprising the steps of irradiating a transparent object with light and inspecting the surface or interior of the transparent object, wherein transmitted light is observed on the side of the transparent object that is opposite to a light source.

Through observation of transmitted light having passed through a transparent object, the eyes of an inspector are not dazzled, in contrast with the case of observing reflected light from the surface of a transparent object; thus, the eyes are not burdened with light, the inspector does not overlook defects, and excellent detection accuracy and improved inspection efficiency are provided.

Preferably, the observation for inspection is performed visually. Also, preferably, the inspection is performed to detect foreign matter present in the surface or interior of the transparent object.

When a transparent object is to be visually inspected for foreign matter present on the surface or in the interior of the transparent object, the method of the invention is particularly effective because the eyes of an inspector are not dazzled by light. Further, foreign matter can be readily detected more accurately than in the case of mechanical detection, for example, detection through use of an He—Ne-laser-type foreign matter inspection machine.

Further, preferably, the transparent object to be inspected is a pellicle membrane.

Through application to the inspection of a pellicle membrane, which must have particularly high transparency and must not carry even foreign matter as small as that on the submicron order, the inspection method of the invention exhibits its effectiveness.

According to a second aspect of the present invention, there is provided an inspection apparatus for a transparent object, comprising: transparent-object-moving means for moving a transparent object to an inspection position and for fixing the transparent object in the inspection position; irradiation means for emitting light from a light source disposed on one side of the transparent object so as to irradiate light onto the transparent object fixed in the inspection position by the transparent-object-moving means; and detection means located on the side of the transparent object opposite the light source and having a detector for detecting light that has been emitted from the light source and has passed through the transparent object.

The inspection apparatus enables an inspector to inspect a transparent object for foreign matter in a nonvisual manner and to accurately inspect a number of transparent objects in a short period of time.

Preferably, the detector is a CCD camera.

When, for example, a pellicle is to be inspected for foreign matter, the employment of a CCD camera as the detector enables the inspection of the portion of a pellicle membrane in the vicinity of and along a pellicle frame as in the case of visual inspection.

Preferably, the CCD camera as the detector is a digital CCD camera having a quantum efficiency of not less than 10%, a full well capacity of not less than 30,000 electrons, and a gradation number of not less than 256.

The above property ranges are specified for the CCD camera, because when the quantum efficiency indicative of sensitivity, the full well capacity indicative of dynamic range, and the gradation number indicative of resolution for quantity of light are in the above-described ranges, the digital CCD camera exhibits balanced performance and good detection efficiency when used as the detector.

Examples of such a digital CCD camera include digital cooled CCD cameras and digital CCD line-sensor cameras.

Further, preferably, the detector is positioned such that it is not directly irradiated with a bundle of rays from the light source of the irradiation means.

Through such positioning of the detector, a CCD camera, when used as the detector, does not suffer saturation of electric charge, and thus an inspection for foreign matter can be performed accurately.

Needless to say, the position of irradiating a transparent object with a bundle of rays from the light source of the irradiation means, i.e. a portion to be inspected, must be located within the detection range of the detector. Otherwise, no foreign matter can be detected; in other words, the inspection apparatus fails to achieve the expected function.

Preferably, the detector detects transmitted light which has passed through a transparent object to be inspected and has been scattered by foreign matter present on the surface or in the interior of the transparent object.

In the inspection apparatus of the present invention, foreign matter present on the surface or in the interior of a transparent object is irradiated with light which is emitted from the light source and passes through the transparent object, and light scattered by the foreign matter is detected by the detector.

Preferably, the transparent object to be inspected by the inspection apparatus of the present invention is a pellicle membrane.

Further, preferably, the light source is a high-intensity halogen lamp having a luminance of not less than 5,000 lux.

Through use of a high-intensity halogen lamp as the light source, a transparent object can be irradiated with light over a relatively wide area, and relatively high uniform illuminance can be obtained. Thus, the transparent object can be inspected more efficiently than in the case of inspection through use of laser beam.

According to a third aspect of the present invention, there is provided an inspection system for a transparent object, comprising: (a) an inspection apparatus section comprising an inspection apparatus according to the second aspect; (b) a control section for controlling the transparent-object-moving means, irradiation means, and detection means of the inspection apparatus section; (c) an image processing section for image-processing light detected by the detection means; (d) an analyzing section for providing the control section with information about control of the positions of the transparent-object-moving means, the irradiation means, and the detection means and for analyzing the result of processing conducted in the image processing section; and (e) an inspection result display section for displaying the result of analysis conducted in the analyzing section.

Through employment of the inspection system, light detected by the detector of the inspection apparatus section undergoes image-processing in the image processing section, and the result of the image processing is analyzed in the analyzing section, so that the result of the analysis, i.e. the size, amount, and position of foreign matter located in a transparent object, can be displayed on the inspection result display section in the form of a map. From the data displayed on the inspection result display section, an inspector can readily judge whether the inspected transparent object is usable, whether foreign matter must be removed, or from what position foreign matter must be removed.

Also, for reasons similar to those mentioned in relation to the inspection apparatus of the present invention, the detector of the inspection apparatus section is preferably a CCD camera. More preferably, the CCD camera used as the detector is a digital CCD camera. Particularly preferably, the digital CCD camera has a quantum efficiency of not less than 10%, a full well capacity of not less than 30,000 electrons, and a gradation number of not less than 256.

Also, preferably, the detector of the inspection apparatus section is positioned such that it is not directly irradiated with a bundle of rays from the light source of the inspection apparatus section.

Through such positioning of the detector, the detection accuracy of the detection means is improved. Also, in this case, the position where a transparent object is irradiated with light from the light source must be located within the detection range of the detection means.

According to the inspection method for transparent objects of the present invention, an inspector visually observes transmitted light which has passed through a transparent object on the side opposite to the light source with respect to the pellicle; thus, the inspector's eyes are not dazzled by light. Accordingly, the inspector can readily find fine foreign matter, if any, so that highly accurate inspection can be carried out in a reduced period of time. Further, the burden on the inspector's eyes is reduced, and inspection efficiency is significantly improved.

Further, according to the inspection apparatus and inspection system for transparent objects of the present invention, a transparent object can be inspected for foreign matter present on the surface or in the interior of the transparent object without use of reflected light. Accordingly, a number of transparent objects can be inspected without foreign matter being overlooked. Thus, the present invention enables a user to conduct highly accurate inspection of transparent objects.

DESCRIPTION OF THE INVENTION AND PREFERRED EMBODIMENTS

The present invention and embodiments thereof will now be described in detail with reference to the drawings. However, the present invention is not limited thereto.

According to a conventional inspection method in which a pellicle membrane is inspected through observation of light reflected from the pellicle membrane, a burden on the eyes of an inspector is heavy, detection limit is relatively coarse, and inspection efficiency is relatively low. The inventors of the present invention conducted extensive studies in an attempt to improve the conventional inspection method and found that there can be readily and promptly carried out a highly accurate inspection of a pellicle membrane for foreign matter present on the surface and in the interior of the pellicle membrane through visual observation of transmitted light which has passed through the pellicle membrane, thus achieving the invention.

The inspection method of the present invention will now be described with reference to FIG. 1, taking an example of inspection of a pellicle membrane.

Figure 1:
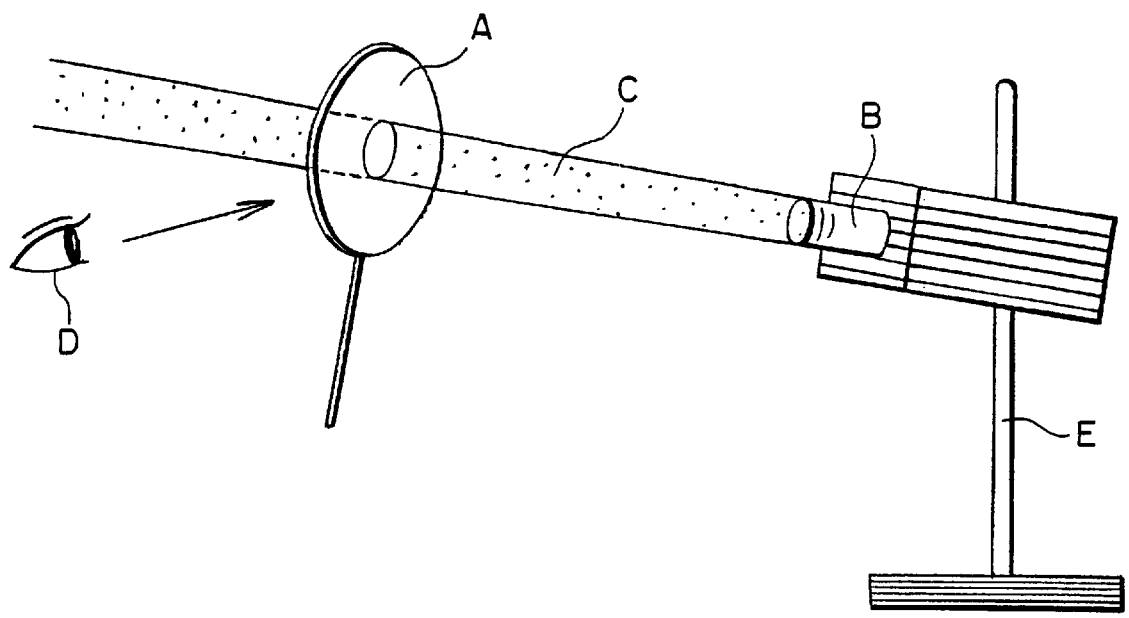
FIG. 1 is a view illustrating an inspection method of the present invention.

As shown in FIG. 1, in a darkroom, a pellicle, which is composed of a pellicle frame and a pellicle membrane A bonded onto the frame, is positioned perpendicularly to the optical path C of spot-light emitted from a convergence lamp B attached to a stand E, and transmitted light which has passed through the pellicle membrane A is observed by eyes D in a position located outside the optical path C of transmitted light. In contrast with observation of reflected light, observation from outside the optical path does not cause the eyes D to be dazzled by light. Thus, the inspector can readily detect fine foreign matter or the like present on the surface or in the interior of the pellicle membrane A in a short period of time.

Figure 5:
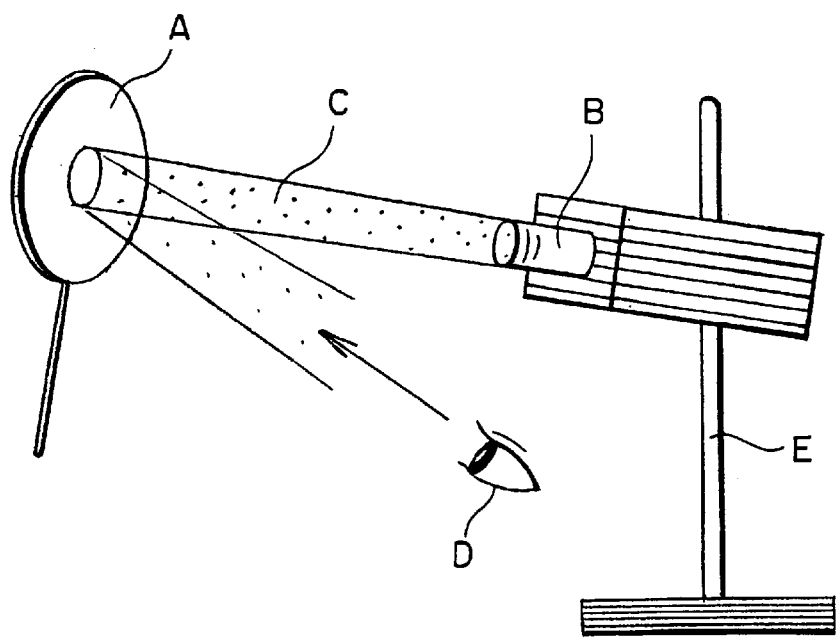
FIG. 5 is a view illustrating a conventional inspection method.

As shown in FIG. 5, in a conventional inspection method, a pellicle membrane A is irradiated with a spot-light C, and light reflected from the pellicle membrane A is observed to thereby detect foreign matter present on the surface or in the interior of the pellicle membrane A. However, since an inspector is situated on the same side as that on which the spot-light C is reflected, light reflected from the pellicle membrane A or from a pellicle frame directly impinges on the eyes D of the inspector. Thus, the inspector is dazzled and unable to detect fine foreign matter, and afterimage in the eyes impairs inspection efficiency; specifically, inspection takes 3 to 4 minutes per pellicle. Also, there result variations in inspection accuracy among inspectors.

In the inspection method of the present invention, light does not directly impinge on the eyes of an inspector and thus does not dazzle the eyes, thereby reducing a burden on the eyes. Accordingly, the illuminance of a convergence lamp can be increased in comparison with the case of the conventional method. Thus, finer foreign matter is likely to be detected in a shorter period of time, specifically, approximately 1 minute and a half per pellicle, which is approximately half the time of inspection required in the conventional method. Hence, inspection efficiency is significantly improved.

Also, because of the capability of utilizing light scattered forward from foreign matter present on the surface or in the interior of a transparent object, the inspection method of the present invention can readily detect finer foreign matter (having sizes on the order of submicron) than can the conventional method which utilizes reflected light (backward scattered light) in detection. Specifically, the inspection method of the present invention has been found capable of detecting foreign matter as small as approximately 0.1 to 0.2 $\mu$m. That is, while the detection limit of the conventional inspection method is said to be approximately 0.3 $\mu$m, that of the inspection method of the present invention is improved to 0.2 $\mu$m, indicating that the inspection method of the present invention is very effective for improving quality of a pellicle membrane.

In the inspection method of the present invention, the wavelength of a light source is not particularly limited. However, since inspection is primarily carried out visually, the light source is preferably of visible light. Examples of the light source include high-intensity halogen lamps and xenon lamps. Inspection illuminance is not particularly limited, but is approximately 50,000 to 1,000,000 lux.

In the inspection method of the present invention, a photo-detection device is not particularly limited so long as light scattered by foreign matter present on the surface or in the interior of a transparent object can be detected. However, the photo-detection device is most preferably the eyes of an inspector having high detection accuracy and high capability of judging whether the inspected transparent object is usable. Since an inspector observes transmitted light, the inspector's eyes are not dazzled by light; thus, the inspector can continue inspection work for a longer period of time, and detection accuracy is improved as mentioned above.

As a photo-detection device other than the eyes of an inspector, a photo-detection element may be selected as adequate in accordance with a light source to be used, the type of a transparent object to be inspected, or detection accuracy. Automatic inspection is also feasible. Examples of a photo-detection device other than the eyes of an inspector include those utilizing CdS elements or CCD for detection of visible light. The photo-detection device is preferably a digital CCD camera, particularly preferably a digital CCD camera having a quantum efficiency of not less than 10%, a full well capacity of not less than 30,000 electrons, and a gradation number of not less than 256.

Examples of such a digital CCD camera include digital cooled CCD cameras and digital CCD line-sensor cameras.

The eyes of an inspector or a photo-detection device may be located in any position so long as they are located outside the path of transmitted light, but is preferably located within a circular cone having an angle $\theta$ of greater than 0°, but not greater than 90° ($0° < \theta \leq 90°$) to the path of transmitted light while its axis is aligned with the optical path.

Next will be described the inspection apparatus and inspection system for transparent objects of the present invention. However, the present invention is not limited thereto as in the case of the inspection method described above.

For example, in the description below, a transparent object is a pellicle, but is not limited thereto. The pellicle is a mere example.

The inventors of the present invention conducted extensive studies in an attempt to solve various problems involved in conventional mechanical inspection, for example, a problem that when a pellicle is irradiated with a laser beam so as to detect light scattered by foreign matter by means of a photomultiplier, the portion of the pellicle in the vicinity of or along a pellicle frame cannot be observed due to the interference of the laser beam with the frame or the diffraction of the laser beam. Based on their new findings, the present invention has been achieved.

First, the inspection apparatus of the present invention will be described with reference to FIG. 2.

Figure 2:
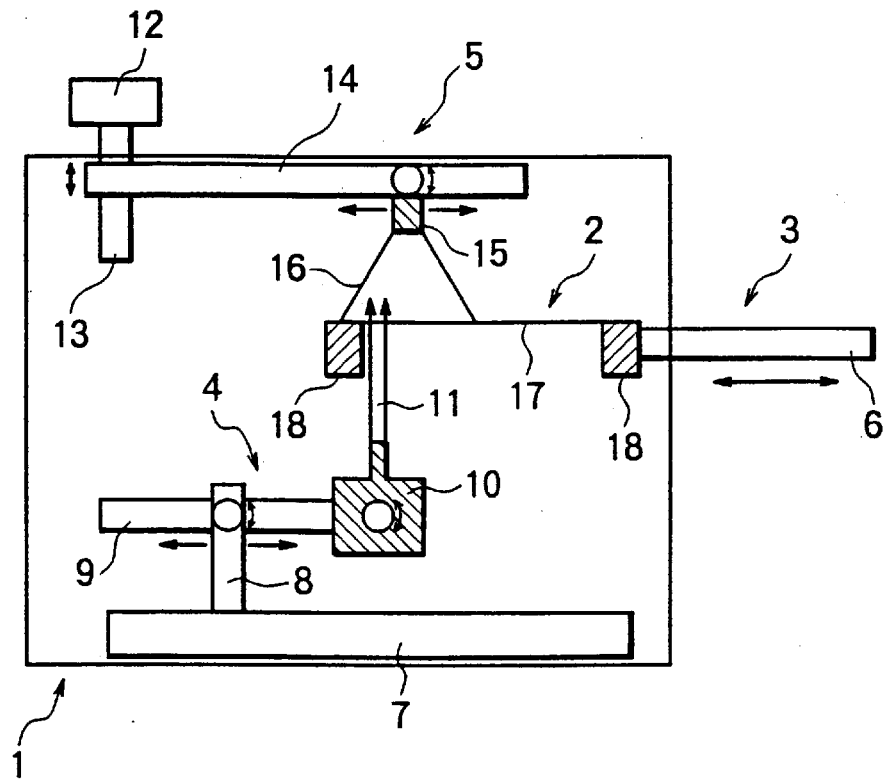
FIG. 2 is a schematic view showing the configuration of an inspection apparatus of the present invention.

In FIG. 2, an inspection apparatus 1 includes transparent-object-moving means 3 for moving a pellicle 2 to be inspected into the inspection apparatus 1 and for securing the pellicle 2 in an inspection-position; irradiation means 4 located on one side of the pellicle 2 (under the pellicle 2 in FIG. 2) secured in an inspection position by the transparent-object-moving means 3; and detection means 5 located on the other side of the pellicle 2.

The transparent-object-moving means 3 includes an unillustrated transparent-object holder and a moving robot 6 for moving the held pellicle 2.

The moving robot 6 is not particularly limited so long as it can move the pellicle 2 into the inspection apparatus 1 and to a predetermined inspection position located between the irradiation means 4 and the inspection means 5 within the inspection apparatus 1 and can secure the pellicle 2 in the inspection position. Also, the transparent-object holder is not particularly limited so long as it can hold the pellicle 2 (transparent object) onto the moving robot 6. In the present embodiment, a pellicle frame 18 is held by the transparent-object holder, and the pellicle 2 is horizontally moved by the moving robot 6.

The irradiation means 4 includes a fixture base 7 for securing the irradiation means 4 within the inspection apparatus 1; a light source support bar 8 standing upright from the fixture base 7; a light source support arm 9 attached to the top end portion of the light source support bar 8; and a light source 10 attached to one end of the light source support arm 9.

The light source support bar 8 is mounted on the fixture base 7 in a manner turnable about its own axis. The light source support arm 9 is attached to the light source support bar 8 slidably along its own axis and in a vertically turnable manner. Also, the light source 10 is attached to the light source support arm 9 in a vertically and horizontally turnable manner so that the pellicle 2 can be irradiated with a bundle 11 of rays in every direction. Accordingly, the light source 10 can move to every required position on one side of the pellicle 2 in order to inspect the pellicle 2 and can emit the bundle 11 of rays in every required angle in order to inspect the pellicle 2.

Herein, a bundle of rays refers to that which is emitted linearly from a light source and is free of any intermediate scatter.

In the present invention, the light source 10 is not particularly limited so long as it can emit light detectable by the detector of the detection means 5, which will be described later. Examples of the light source 10 include halogen lamps and xenon lamps. The light source 10 is preferably a high-intensity halogen lamp, which can irradiate an object with a bundle of rays over a relatively wide range of area, can provide a relatively high, uniform illuminance, and enables higher inspection efficiency as compared with the case of a laser beam, and particularly preferably a high-intensity halogen lamp having a luminance of not less than 5,000 lux because illuminance required for inspection is not less than 5,000 lux.

Further, in order to reduce inspection time and improve inspection accuracy, illuminance is preferably 10,000 to 1,000,000 lux. Accordingly, particularly preferably, a light source used in the present invention provides such an intensity of illuminance.

In the present invention, the irradiation means 4 is not particularly limited to the above-mentioned example, but may be of any type so long as the light source 10 can be brought to a required position for inspection and the bundle 11 of rays can be emitted in any required direction for inspection.

For example, the fixture base 7 may be movable in order to move the light source 10.

Next, the detection means 5 will be described. The detection means 5 includes a fixture section 12 for securing the detection means 5; a detector support bar 13 standing from the fixture section 12; a detector support arm 14 one end of which is attached to the detector support bar 13; and a detector 15 attached to the detector support arm 14.

The detector support bar 13 is attached to the fixture section 12 slidably in a direction perpendicular to the plane of the paper of FIG. 2. The detector support arm 14 is attached to the detector support bar 13 slidably in the axial direction of the detector support bar 13. The detector 15 is attached to the detector support arm 14 slidably in the axial direction of the detector support arm 14 as well as in a vertically and horizontally turnable manner so that its detection range 16 of the detector 15 can face the pellicle 2 in every direction. Accordingly, the detector 15 can move to any position in order to detect light scattered by foreign matter present in the pellicle 2 irradiated with light from the light source 10 and can orient its detection range 16 of the detector 15 in any direction in order to detect light scattered by foreign matter.

The detector 15 is not particularly limited, but may be selected as appropriate in accordance with the type of a light source to be used, the type of a defect to be detected, or detection accuracy. The detector 15 is preferably a CCD camera, which can inspect the portion of the pellicle 2 in the vicinity of or along the pellicle frame 18 and facilitates subsequent data processing, particularly preferably a digital CCD camera.

Preferably, the digital CCD camera has a quantum efficiency of not less than 10%, a full well capacity of not less than 30,000 electrons, and a gradation number of not less than 256.

The above property ranges are specified for the digital CCD camera, because when the quantum efficiency indicative of sensitivity, the full well capacity indicative of dynamic range, and the gradation number indicative of resolution for differential quantity of light (AD unit=full well capacity divided by a gradation number) are in the above-described respective ranges, the digital CCD camera exhibits balanced performance and good detection efficiency when used as the detector.

Specific examples of such a digital CCD camera include digital cooled CCD cameras (for example, C4880-16 (trade name, product of Hamamatsu Photonics)) and digital CCD line-sensor cameras (for example, TECHNOS 3000H (trade name, product of Technos)).

In the present invention, the detection means 5 is not limited to the above-mentioned embodiment, but may be of any type so long as the detector 15 can be moved to a required detection position and the detection range 16 of the detector 15 can be oriented in a required direction for detection of light scattered by foreign matter.

For example, the fixture section 12 may be movable in order to move the detector 15 to a required detection position, and the detector support bar 13 may turn about its own axis to thereby move the detector 15.

Next, inspection of a pellicle through use of the inspection apparatus of the present invention will be described with reference to FIG. 2.

First, the pellicle 2 to be inspected is held onto the moving robot 6 by means of the transparent-object holder of the transparent-object-moving means 3. The moving robot 6 moves the pellicle 2 to a predetermined inspection position within the inspection apparatus 1 and secures the pellicle 2 in the position.

The light source 10 is moved to a predetermined position through movement of the light source support bar 8 and light source support arm 9. Then, the light source 10 is turned so as to irradiate a portion to be inspected on the pellicle membrane 17 of the pellicle 2 with the bundle 11 of rays from the light source 10.

Next, the detector 15 is moved to a position located slightly off the bundle 11 of rays from the light source 10 (a position where the detector 15 is not directly irradiated with the bundle 11 of rays from the light source 10) through the sliding operation of the detector support bar 13 on the fixture section 12, the sliding operation of the detector support arm 14 along the detector support bar 13, and the sliding operation of the detector 15 along the detector support arm 14. Further, the detector 15 is turned so that a portion to be inspected on the pellicle membrane 17 enters the detection range 16 of the detector 15.

Through the establishment of the above arrangement for detection, the detector 15 is not directly irradiated with the bundle 11 of rays from the light source 10. Accordingly, when the detector 15 is, for example, a CCD camera, no saturation of electric charge occurs, so that the CCD camera can accurately detect light scattered by foreign matter present on the surface or in the interior of the pellicle membrane 17.

Figure 3:
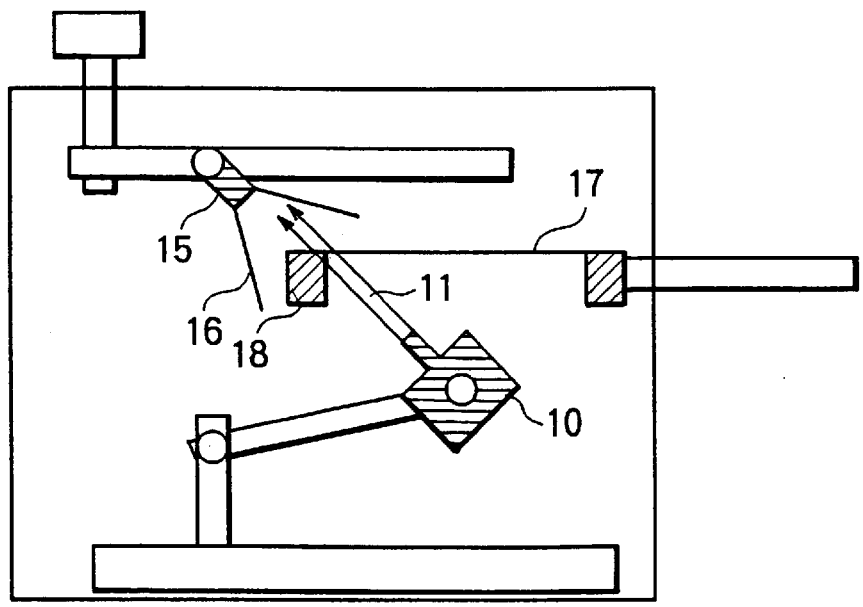
FIG. 3 is a schematic view showing a certain phase of operation of the inspection apparatus.

Also, as shown in FIG. 3, when the bundle 11 of rays from the light source 10 intersects the pellicle frame 18 in order to inspect the portion of the pellicle membrane 17 in the vicinity of the pellicle frame 18, the detector 15 is arranged such that the light source 10, an inspection spot on the pellicle membrane 17 (a spot at which the pellicle membrane 17 is irradiated with the bundle 11 of rays), and the detector 15 are substantially aligned with each other. However, in this case, the detector 15 is arranged so as not to be directly irradiated with the bundle 11 of rays, through the interception of the bundle 11 of rays by the pellicle frame 18. Next, the detector 15 is turned so as to bring the inspection spot on the pellicle membrane 17 into the inspection range 16 of the detector 15.

Through the establishment of the above arrangement for detection, even when the bundle 11 of rays from the light source 10 impinges on the pellicle frame 18, light reflected from the pellicle frame 18 does not cause an impairment of detection accuracy of the detector 15 (for example, the saturation of electric charge in the case where the detector 15 is a CCD camera). Also, there can be established high contrast between light scattered by the pellicle frame 18 and light scattered by foreign matter present on the surface or in the interior of the pellicle membrane 17; thus, light scattered by the pellicle frame 18 do not raise a serious problem in detection of foreign matter.

Finally, the inspection system for transparent objects of the present invention will be described with reference to FIG. 4.

Figure 4:
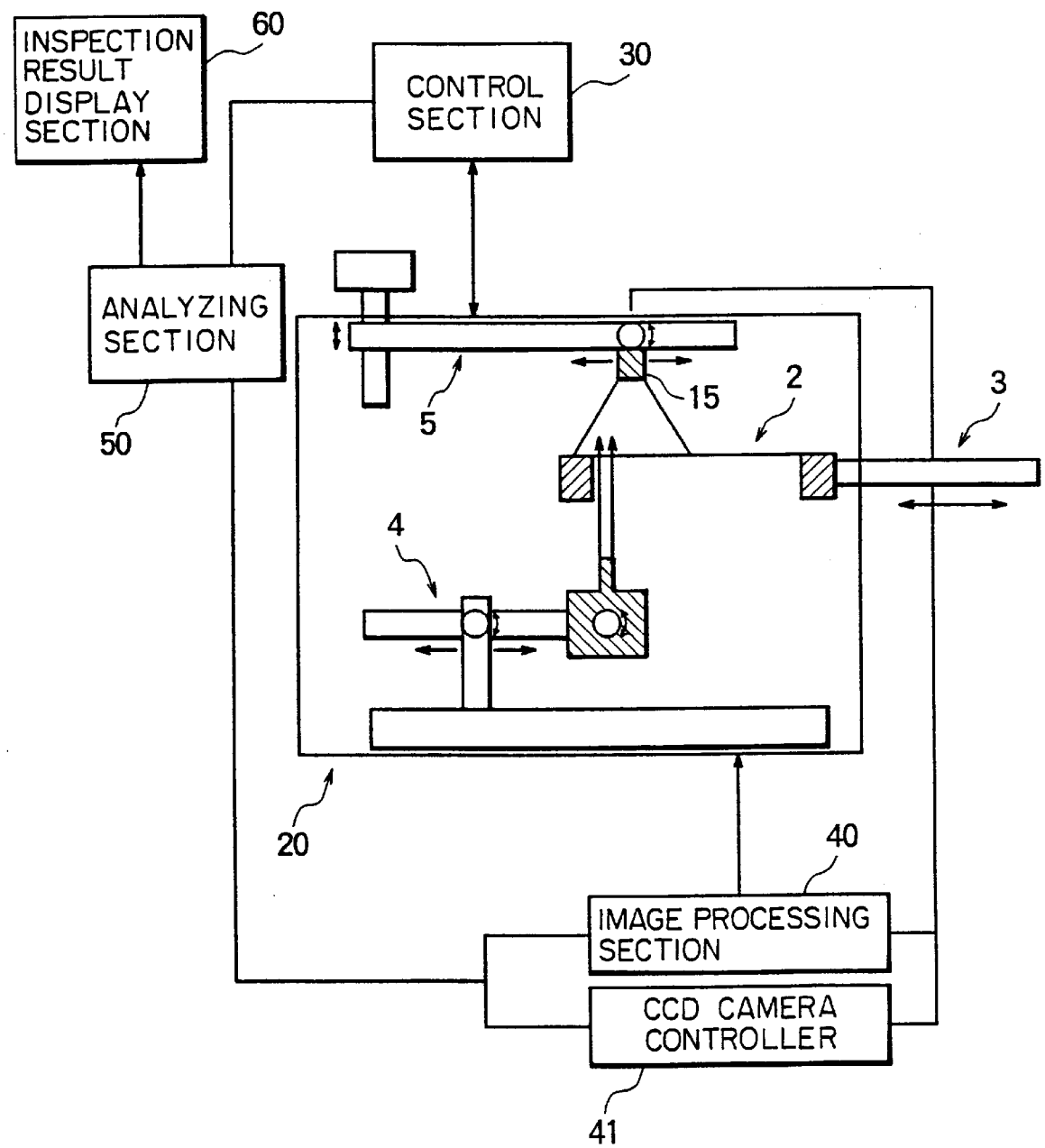
FIG. 4 is a block diagram showing an inspection system of the present invention.

In FIG. 4, reference numeral 20 denotes an inspection apparatus section including the above-described inspection apparatus of the present invention. The transparent-object-moving means 3, irradiation means 4, and detection means 5 of the inspection apparatus section 20 are controlled by a control section 30. After being detected by the detector 15 of the inspection apparatus section 20, light scattered by foreign matter present in the pellicle 2 undergoes image processing in an image processing section 40, whereby intensity of the scattered light is recorded. Further, from the positional relation among the means of the inspection apparatus section 20, the position of foreign matter on the pellicle 2 is determined.

Since the present embodiment uses a CCD camera as the detector 15, a CCD camera controller section 41 is provided in order to control the CCD camera (detector 15).

The result of image processing is sent to an analyzing section 50 and analyzed therein. The analyzing section 50 retains information about the optimum positional relation for inspection among the transparent-object-moving means 3, the irradiation means 4, and the detection means 5. Upon start of inspection, the analyzing section 50 calculates an optimum positional relation among the means based on the retained information and sends the thus-obtained information about the optimum positional relation to the control section 30, which, in turn, controls the positions of the means so as to optimize the relative position among the means.

The result of analysis conducted by the analyzing section 50 is displayed on an inspection result display section 60 in the form of, for example, map, which gives information about, for example, the position and size of foreign matter present in the pellicle 2.

Relevant computers are usually employed to serve as the control section 30, the image processing section 40, the analyzing section 50, and the inspection result display section 60. In this case, the computer employed as the analyzing section 50 serves as a host computer.

EXAMPLES

The inspection method of the present invention will now be described by way of example.

Example

A darkroom capable of completely shutting outside light out was built within a clean room (class: 1–10). The interior of the darkroom was sustained at a cleanliness level similar to that of the clean room. The internal space of the darkroom was determined so as to be sufficient for inspection and such that inspection light emitted from the light source do not disturb inspection itself.

The spot type high-intensity halogen lamp, YP-150-1 (trade name, product of Yamada Kogaku), was used as the light source for inspection and installed on the inspection base. The illuminance of the light source was set to 500,000 lux. A transparent object to be inspected was a pellicle for use in semiconductor lithography. The pellicle was placed in the path of light emitted from the lamp and oriented perpendicular to the optical path. The membrane of the pellicle was visually inspected for foreign matter on the side opposite to the light source with respect to the pellicle. 18 pellicles were inspected. The result is shown in Table 1.

Comparative Example 1

Each of the pellicles used in the Example was placed in the optical path and inspected in accordance with a conventional inspection method. Specifically, the membrane of the pellicle was visually inspected for foreign matter on the same side as that on which light is reflected, i.e., on the same side as that of the light source with respect to the pellicle. The 18 pellicles used in the Example were inspected. The result is shown in Table 1.

Comparative Example 2

The pellicles which had been visually inspected were inspected through use of the He—Ne-laser-type foreign matter inspection apparatus. In inspection, light reflected from foreign matter was detected by the photo-detection device to thereby obtain the size and quantity of foreign matter. The result is shown in Table 1.

TABLE 1

| Sample No. | Example [Inspection method of present invention] Quantity of foreign matter (pieces) A | Comp. Example 1 [Conventional inspection method] Quantity of foreign matter (pieces) B | Differences in detected quantity of foreign matter (pieces) A − B | Comp. Example 2 [Foreign matter inspection apparatus] Quantity of foreign matter (pieces) | |
|---|---|---|---|---|---|
| | | | | 0.3–0.5 μm | Not less than 0.5 μm |
| 1 | 1 | 1 | 0 | 1 | 0 |
| 2 | 0 | 0 | 0 | 0 | 0 |
| 3 | 2 | 1 | +1 | 1 | 0 |
| 4 | 4 | 3 | +1 | 2 | 1 |
| 5 | 2 | 2 | 0 | 2 | 0 |
| 6 | 0 | 0 | 0 | 0 | 0 |
| 7 | 4 | 1 | +3 | 1 | 0 |
| 8 | 1 | 1 | 0 | 1 | 0 |
| 9 | 2 | 1 | +1 | 1 | 0 |
| 10 | 1 | 0 | +1 | 0 | 0 |
| 11 | 6 | 4 | +2 | 3 | 1 |
| 12 | 3 | 2 | +1 | 2 | 0 |
| 13 | 4 | 3 | +1 | 2 | 1 |
| 14 | 6 | 5 | +1 | 4 | 1 |
| 15 | 2 | 2 | 0 | 1 | 1 |
| 16 | 1 | 1 | 0 | 1 | 0 |
| 17 | 0 | 0 | 0 | 0 | 0 |
| 18 | 1 | 1 | 0 | 1 | 0 |
| Total | 40 | 28 | +12 | 23 | 5 |

As seen from Table 1, the conventional method which uses reflected light for inspection shows a detection limit of 0.3 μm, whereas the inspection method of the present invention which uses transmitted light for inspection enables an inspector to detect foreign matter having a size of not greater than 0.3 μm.

The present invention is not limited to the above-described embodiments. The above-described embodiments are mere examples, and those having the substantially same structure as that described in the appended claims and providing the similar action and effects are included in the scope of the present invention.

For example, the above embodiments are described while mentioning a pellicle membrane as a transparent object. However, the present invention is not limited thereto. Examples of a transparent object include quartz substrates for semiconductor devices, photomasks bearing semiconductor circuit patterns formed thereon, optical lenses, and optical cells. According to the present invention, such transparent objects can be highly accurately inspected for various kinds of defects present on the surface or in the interior thereof, such as scratches, flaws, bubbles, protrusions, dimples, deformations, and other optically detectable defects.

What is claimed is:

1. An inspection system for a pellicle membrane comprising:
    (a) an inspection apparatus section comprising:
        (i) a moving mechanism for moving the pellicle membrane to an inspection position and for fixing the pellicle membrane in the inspection position;
        (ii) a single light source disposed on one side of the pellicle membrane so as to irradiate light onto the pellicle membrane fixed in the inspection position by said moving mechanism; and
        (iii) a detection device located on the side of the pellicle membrane opposite the single light source in a position that is not directly irradiated with a bundle of rays from the single light source and having a detector for detecting light that has been emitted from the single light source and has passed through the pellicle membrane;
    (b) a control section for controlling the moving mechanism, single light source, and detection device of said inspection apparatus section;
    (c) an image processing section for image-processing light detected by said detection device;
    (d) an analyzing section for providing said control section with information about control of the positions of said moving mechanism, said single light source, and said detection device and for analyzing the result of processing conducted in said image processing section; and
    (e) an inspection result display section for displaying the result of analysis conducted in said analyzing section;
    wherein based on information from said analyzing section, said control section controls the positional relation among said moving mechanism, said single light source, and said detection device in order to position the detector of said detection device such that the detector is not directly irradiated with a bundle of rays from the single light source.

2. A method for inspecting a portion of a pellicle membrane which is in the vicinity of a pellicle frame, said pellicle frame having opposite first and second sides thereof and the pellicle membrane being mounted on the first side of said frame, comprising:
    (i) positioning a light source, a light detector and a pellicle, said pellicle consisting of said pellicle membrane and said pellicle frame, such that said light source and said light detector are on the opposite side from each other across said pellicle and such that said light detector is adjacent the first side of said frame and said light source is adjacent the second side of said frame;
    (ii) positioning said detector within an angle included between a path of a light from said light source and said pellicle membrane, but not on the light path or a plane including the membrane;
    (iii) irradiating said pellicle membrane with light from said light source; and
    (iv) inspecting the surface or interior of said membrane by observing said transmitted light.

* * * * *